United States Patent
Bhushan et al.

(10) Patent No.: US 9,044,505 B2
(45) Date of Patent: Jun. 2, 2015

(54) MULTIMERIC BIOTINIDASE RESISTANT MULTIMODALITY PROBES

(71) Applicants: Kumar Ranjan Bhushan, St. Louis, MO (US); Preeti Misra, St. Louis, MO (US)

(72) Inventors: Kumar Ranjan Bhushan, St. Louis, MO (US); Preeti Misra, St. Louis, MO (US)

( * ) Notice: Subject to any disclaimer, the term of this patent is extended or adjusted under 35 U.S.C. 154(b) by 0 days.

(21) Appl. No.: 13/714,341

(22) Filed: Dec. 13, 2012

(65) Prior Publication Data

US 2014/0171627 A1    Jun. 19, 2014

(51) Int. Cl.
*C07F 5/00* (2006.01)
*A61K 49/10* (2006.01)
*A61K 49/00* (2006.01)

(52) U.S. Cl.
CPC ......... *A61K 49/0002* (2013.01); *A61K 49/0052* (2013.01); *A61K 49/108* (2013.01); *A61K 49/106* (2013.01); *A61K 49/0032* (2013.01)

(58) Field of Classification Search
USPC .......................................... 424/9.1
See application file for complete search history.

(56) References Cited

U.S. PATENT DOCUMENTS 6,120,768 A * 9/2000 Griffiths et al. ............ 424/178.1

FOREIGN PATENT DOCUMENTS

WO    WO 9515335 A2 *  6/1995  ............... C07K 1/08

OTHER PUBLICATIONS

Sabatino et al. (J. Med. Chem. 2003, 46, 3170-3173).*

* cited by examiner

*Primary Examiner* — Michael G Hartley
*Assistant Examiner* — Melissa Perreira

(57) ABSTRACT

The present invention describes multimeric multimodality probes. In particular, the present invention discloses (strept) avidin specific multimeric biotinidase resistant multimodality probes.

17 Claims, 7 Drawing Sheets

MULTIMERIC BIOTINIDASE RESISTANT MULTIMODALITY PROBES

FIELD OF THE INVENTION

The present invention discloses (strept)avidin specific multimeric biotinidase resistant multimodality probes.

BACKGROUND

The high affinity (strept)avidin-biotin binding system is widely utilized in pre-clinical diagnostic applications and is under evaluation as a molecular component for imaging and tumor-targeted cancer therapeutic {Rusckowski, 1996; van Gog, 1998}. It is believed that the biotinidase enzyme, which is present in serum and tissue of both animals and humans in nanomolar concentrations, cleave the biotinamide bond linking biotin (vitamin H) and lysine in biocytin, such that this essential vitamin can be recycled {Foulton, 1998; Hymes, 1996}. For in vivo studies, though, targeted biotin derivatives must have serum stability and aqueous solubility {Wilbur, 1997}. The nonspecific nature of the cleavage of biotinamide bonds in biotin conjugates has made it imperative that biotin derivatives employed in vivo be designed in a manner that blocks the enzyme activity.

The multimodality imaging of direct or pre-targeting (strept)avidin-biotin strategy has been elusive. The detection of biotin on molecules is facilitated greatly by the wide variety of (strept)avidin-based technologies exploiting the extremely strong noncovalent interaction of (strept)avidin for biotin, with a $K_a$ of $10^{15}$ M. Usually in a pre-targeting strategy, a monoclonal antibody-(strept)avidin conjugate is injected into a patient, allowed to localize at the tumor over 24-48 h, followed by the clearing of excess reagent from blood and administration of the radiolabeled biotin derivative.

SUMMARY

Multimodality imaging is becoming increasingly common in both the clinic and the laboratory {Park, 2005; Pietrzyk, 1996; Saoudi, 1999}. By combining both anatomical and functional images, one can, for example, localize uptake of a tracer or contrast agent to a particular tissue or organ within a subject. In the clinic, multimodality imaging can be used for the diagnosis of disease, staging to help select between therapies, or to assess the efficacy of a course of treatment. In the laboratory, multimodality imaging is used to correlate genomic and phenomic types, make quantitative data more reliable, quantify the damage due to induced disease states or injuries, and assess the usefulness of treatment options.

Rational for multimodal probes: (a) Nuclear and Optical Probes: Nuclear imaging is an established clinical molecular imaging modality that offers good sensitivity at deep tissue sites. However, nuclear imaging techniques remain limited by several factors such as time-consuming procedures, expensive equipment, need for highly skilled personnel and relatively poor spatial resolution {Weissleder, 2001}. On the other hand, optical imaging is a relatively new molecular imaging modality that offers real-time and high-resolution imaging of fluorophores embedded in diseased tissues {Sokolov, 2003; Ntziachristos, 2003; Gurfinkel, 2003}. Of the various optical imaging techniques investigated to date, near-infrared (NIR, 700-900 nm wavelength) fluorescence-based imaging is of particular interest for noninvasive in vivo imaging because of the relatively low tissue absorption and minimal autofluorescence of NIR light {Ntziachristos, 2003; Gurfinkel, 2003}. Considering the importance and advantages of both nuclear and fluorescence imaging, a combination of these two techniques provides an attractive approach for enhancing the imaging accuracy and providing complementary information for improving diagnosis and management of diseases. The strategy to achieve this goal is to develop an optical and nuclear dual labeled imaging agent.

(b) MR and Optical Probes: In general, optical imaging methods have high sensitivity and are cost effective at the cell/tissue level. However, most optical imaging apparatus lacks the capacity of tomographic image reconstruction, and therefore 3-D localization of signals in intact tissues/organs has rarely been achieved noninvasively {Li, 2004}. Magnetic resonance (MR) imaging offers the advantages of being non-invasive, tomographic, and high resolution. However, MR imaging contrast dependent on endogenous differences in water content and on relaxation time in the tissue of interest. The specificity and sensitivity of MR imaging is enhanced by contrast agents based on paramagnetic metals such as gadolinium. Combining the excellent 3D spatial resolution and unlimited depth penetration of MR imaging with very high sensitivity of NIR imaging should serve to traverse shortcomings of each technology {Massoud, 2003}.

Nature often takes advantage of multimerization to decrease ligand off-rate and improve affinity of cell surface binders {Kitov, 2003; Mammen, 1998}. There is a general need to find suitable scaffolds for the assembly of multiple targeting ligands and contrast agents in hope that multimerization would improve the performance of cancer specific ligands.

Several different multivalent scaffolds have been used successfully in past particularly for applications in carbohydrate/lectin interactions {Lindhorst, 2002; Lundquist, 2002} but also for peptide/protein interactions {Wright, 2001} and in context of tumor targeting {Carlson, 2007; Thumshirn, 2003}. Among these scaffolds are small molecules with few conjugation sites (~2-10) and larger systems like dendrimers {Voegtle, 2007} and polymers {Haag, 2006}.

The high affinity (strept)avidin-biotin binding system is widely utilized in pre-clinical diagnostic applications and is under evaluation as a molecular component for imaging and tumor-targeted cancer therapeutic {Rusckowski, 1996; van Gog, 1998}. It is believed that the DOTA-biotin adducts, formed via an amide bond between the sidearm of biotin and the spacer carrying the chelating moiety, are per se easily hydrolyzable by the serum biotinidase, an enzyme which is also able to break biotinyl peptides {Pispa, 1965; Hymes, 1996}. Different ways have been designed in the past to prevent the recognition at the site of the enzymatic attack (i.e., substitution of the carbon adjacent to the amide NH, alkylation of the amide group, incorporation of d-amino acids at the breaking point of the molecule, etc.) {Wilbur, 1997; Foulton, 1997; Wilbur, 2006; Sabatino, 2003} in order to look for a good compromise between serum stability and high affinity of the compounds toward (strept)avidin. Several synthetic steps were necessary for all these modifications, which, in some cases, resulted in a diminished binding constant with the (strept)avidin pockets. This fact prompted us to design and synthesize in a few steps a conjugatable biotin derivative devoid of the amide target site of the biotinidase.

The present invention describes a development of multimeric biotinidase resistant multimodality probes. For cancer therapeutics and imaging applications, the in vivo stability of labeled biotin derivatives is of major importance to avoid the release of radioisotopes or labeled fragments of the molecule, which may cause non-specific irradiation of normal tissues. Biotinidase blocking of biotinylated compounds are essential for optimal direct or pre-targeting of tumor-targeted cancer therapeutics and imaging. Present invention explores a system that has potential to provide (strept)avidin-biotin based optimal direct or pre-targeting. In particular, the present invention describes a chemical system for the efficient production of a tri-functional agent comprised of a NIR fluorophore for optical imaging, a metal chelate for simultaneous MR/nuclear imaging, and a biotinidase resistant targeting ligand for high affinity (strept)avidin-biotin binding. Multi-functional probes for concurrent imaging applications could traverse shortcomings of each technology and could provide complementary information.

In one aspect of present invention, an organic chelating ligand is reacted with a trifunctional linker moiety, having primary amine and carboxylic acid functional groups, followed by deprotection of one or more functional groups to yield one or more free functional groups. Chelation of a metal ion on one or more free functional groups results in a metal chelate. Conjugation of a NIR fluorophore on a metal chelate results in a NIR dye containing metal chelate conjugated carboxylic acid precursor. Reaction of a biotinidase resistant targeting ligand {Wilbur, 2006; Sabatino, 2003; FIG. 5} with a NIR dye containing metal chelate conjugated carboxylic acid precursor results in a multimodalilty biotinidase resistant contrast agent (FIG. 1). In such aspect, trifunctional linker moiety 2 is amino acid, polymer, or dendrimer. Metal ion, M is independently selected from Cu, Fe, In, Tm, Yb, Y, Gd, Eu, and a lanthanide. R is t-butyl ester, ester, or hydrogen. $R^1$ is Boc, Fmoc, Ac, Cbz, Bz, and Bn. In one embodiment, a biotinidase resistant targeting ligand, $R^2H$ is selected from the group of:

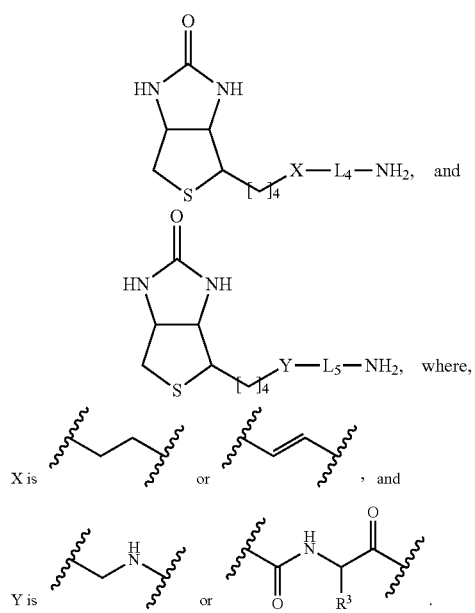

In some embodiments, $L_1$, $L_2$, $L_3$, $L_4$ and $L_5$ are independently selected from alkane, polyethylene glycol, and polypropylene glycol. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, $R^3$ is independently selected from alkyl, alkenyl, alkynyl, phenyl, benzyl, halo, hydroxyl, carbonyl, aldehyde, carboxylate, ester, ether, amine, nitro, nitrile, and pyridyl. In some embodiments, IRDye is a NIR fluorophore independently selected from the group of IRDye 78, IRDye 800CW, IRDye 700DX, VivoTag-S 750, VivoTag 800, VivoTag-S 680, DY-750, DY-682, DY-675, Cypate, Cy7, Alexa Fluor 750, and Alexa Fluor 680.

In an another aspect of present invention, a biotinidase resistant targeting ligand {Wilbur, 2006; Sabatino, 2003; FIG. 5} is conjugated with a multivalent scaffold, followed by deprotection of an amino protecting group to generate an amine containing biotinidase resistant targeting ligand conjugated multivalent scaffold. Reaction of an amine containing biotinidase resistant targeting ligand conjugated multivalent scaffold with a NIR dye containing metal chelate conjugated carboxylic acid precursor 5 (FIG. 1) results in a multimeric multimodalilty biotinidase resistant contrast agent (FIG. 2). In such aspect, $R^1$ is independently selected from Boc, Fmoc, Ac, Cbz, Bz, and Bn. R is t-butyl ester, ester, or hydrogen. M is independently selected from Cu, Fe, In, Tm, Yb, Y, Gd, Eu, and a lanthanide. $R^2$, $R^3$ and $R^4$ are independently selected from:

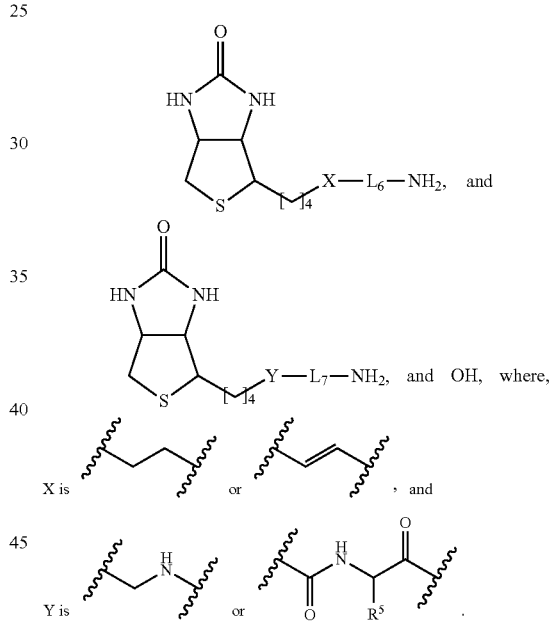

$L_1$, $L_2$, $L_3$, $L_4$, $L_5$, $L_6$, and $L_7$ are linkers independently selected from alkane, amino acid, $-NHCO(CH_2)_5-$, polyethylene glycol, and polypropylene glycol. In one embodiment, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, $R^5$ is independently selected from alkyl, alkenyl, alkynyl, phenyl, benzyl, halo, hydroxyl, carbonyl, aldehyde, carboxylate, ester, ether, amine, nitro, nitrile, and pyridyl. In some embodiments, IRDye is a NIR fluorophore independently selected from the group of IRDye 78, IRDye 800CW, IRDye 700DX, VivoTag-S 750, VivoTag 800, VivoTag-S 680, DY-750, DY-682, DY-675, Cypate, Cy7, Alexa Fluor 750, and Alexa Fluor 680.

The present invention describes multimeric multimodality probes. Particularly, the present invention discloses (strept) avidin specific multimeric biotinidase resistant multimodality probes. Mulimodality probes of present invention provide complementary information. The major medical application of present invention is in direct or pre-targeted diagnosis and therapy of tumors by biotinidase blocking agents. Such technology would improve the therapeutic index of tumor by concentrating target molecule at the tumor site, which also has the benefit of producing fewer toxic side-effects in normal organs.

DETAILED DESCRIPTION

In a present invention, synthetic strategy is developed for multimeric biotinidase resistant multimodality probes for optimal direct or pre-targeting of tumor-targeted cancer therapeutics and imaging. Particularly, present invention describes a chemical system for the efficient production of a tri-functional agent comprised of a NIR fluorophore for optical imaging, a metal chelate for simultaneous MR/nuclear imaging, and a biotinidase resistant targeting ligand for high affinity (strept)avidin-biotin binding. Multimodality probes of present invention allows cross validation and direct comparison between MR/nuclear and NIR optical imaging.

The multimeric biotinidase resistant multimodality probes of present invention are prepared according to the methods known in the art, as illustrated in FIGS. 1-4 and described for specific compounds in examples 1-2. Products are characterized by analytical HPLC, NMR, and LC-MS. Monomeric multimodality probes are obtained in typical yields of 55-65% and trimeric multimodality probes are obtained in typical yields of 25-35%.

Figure 1:
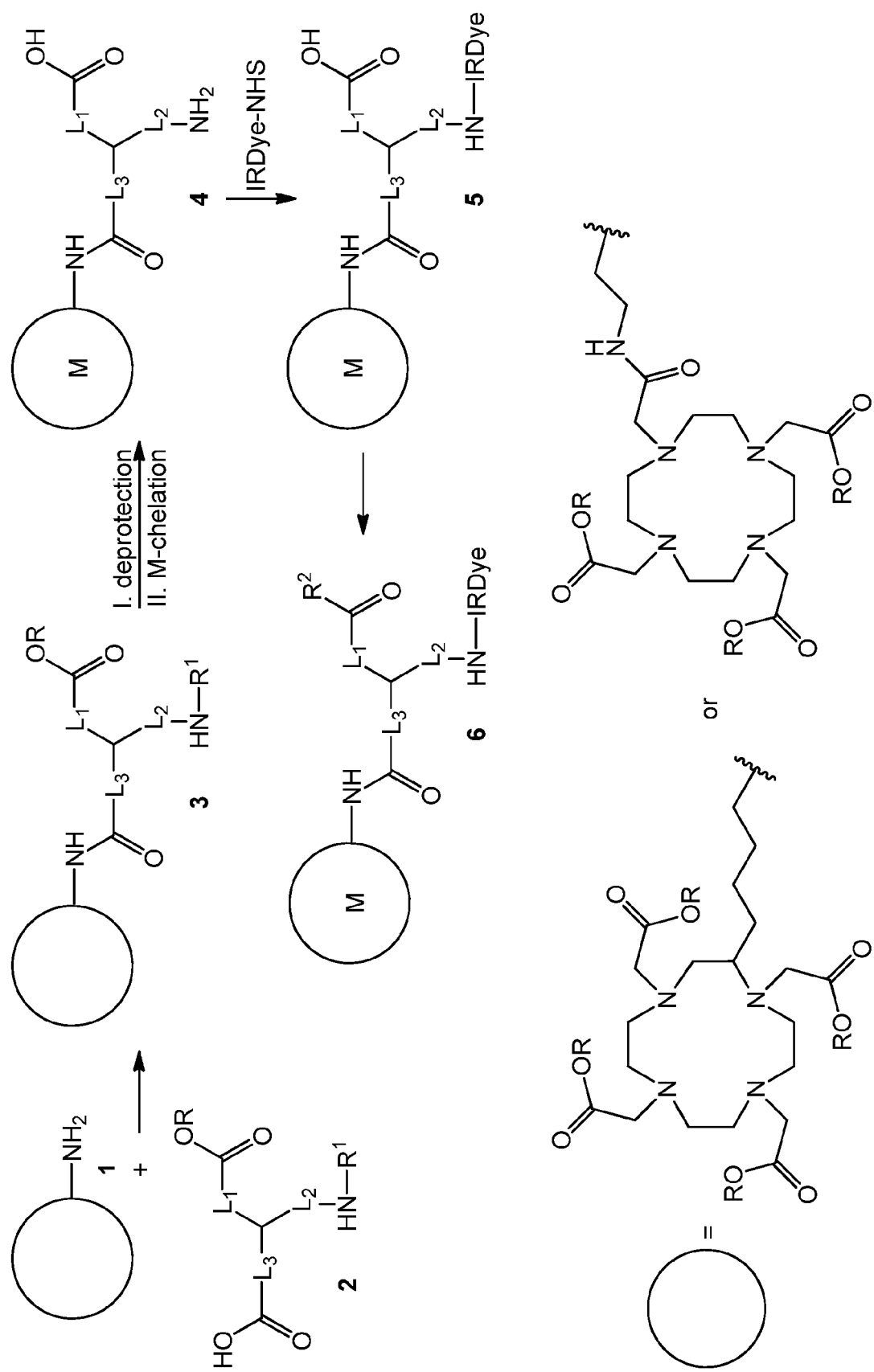
FIG. 1 represents a multimodalilty biotinidase resistant contrast agent in which a NIR fluorophore is conjugated after a metal ion chelation.

FIG. 1 of present invention describes a synthetic scheme for a multimodalilty biotinidase resistant contrast agent in which a NIR fluorophore is conjugated after a metal ion chelation. An organic chelating ligand is reacted with a tri-functional linker moiety, having primary amine and carboxylic acid functional groups, followed by deprotection of one or more functional groups to yield one or more free functional groups. Chelation of a metal ion on one or more free functional groups results in a metal chelate. Conjugation of a NIR fluorophore on a metal chelate results in a NIR dye containing metal chelate conjugated carboxylic acid precursor. Reaction of a biotinidase resistant targeting ligand with a NIR dye containing metal chelate conjugated carboxylic acid precursor to result in a multimodalilty biotinidase resistant contrast agent.

Figure 2:
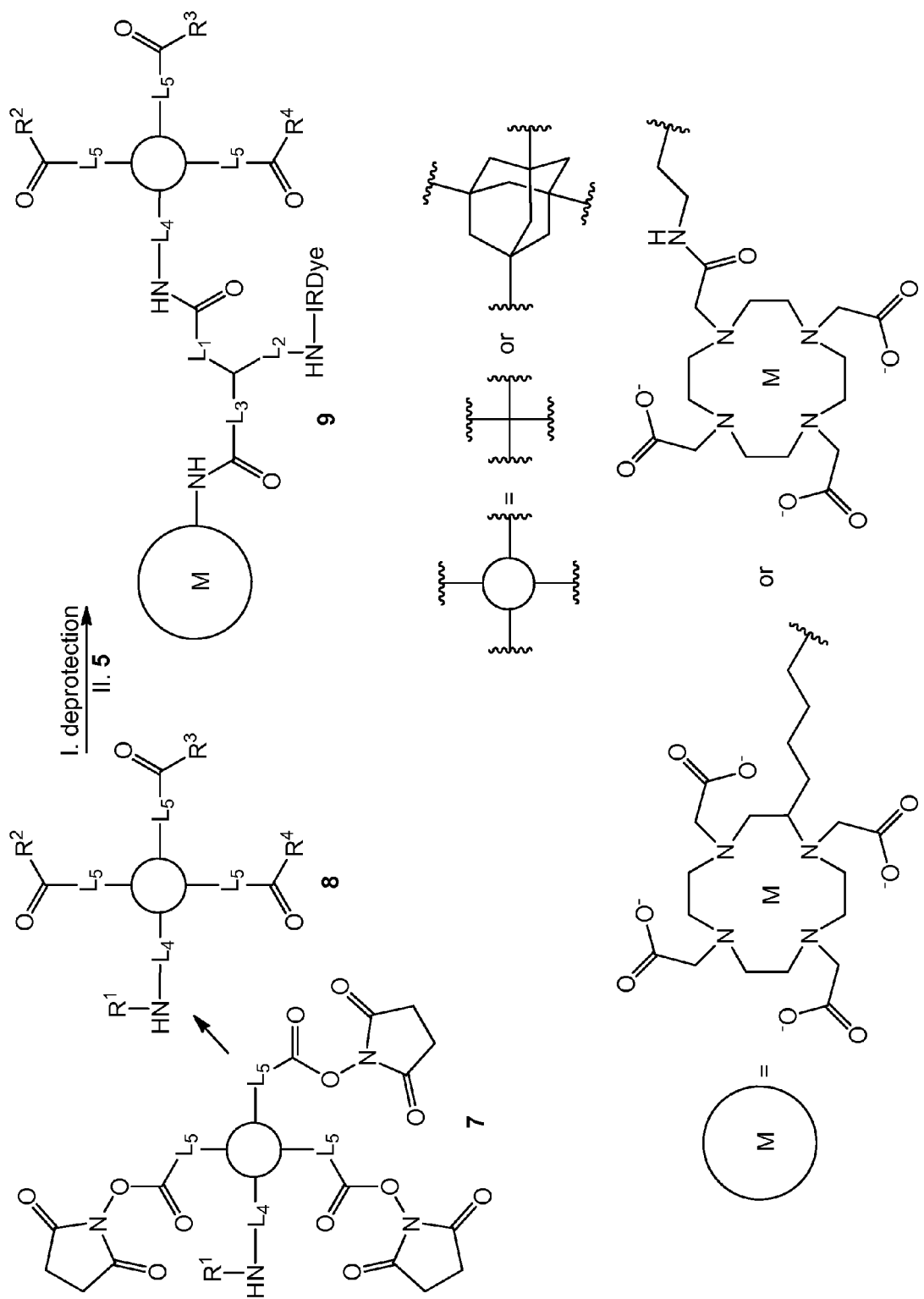
FIG. 2 represents a multimeric multimodalilty biotinidase resistant contrast agent in which a NIR fluorophore is conjugated after a metal ion chelation.

FIG. 2 of present invention describes a synthetic scheme for a multimeric multimodalilty biotinidase resistant contrast agent in which a NIR fluorophore is conjugated after a metal ion chelation. A biotinidase resistant targeting ligand is conjugated with a multivalent scaffold, followed by deprotection of an amino protecting group to generate an amine containing biotinidase resistant targeting ligand conjugated multivalent scaffold. Reaction of an amine containing biotinidase resistant targeting ligand conjugated multivalent scaffold with a NIR dye containing metal chelate conjugated carboxylic acid precursor 5 (FIG. 1) results in a multimeric multimodalilty biotinidase resistant contrast agent.

Figure 3:
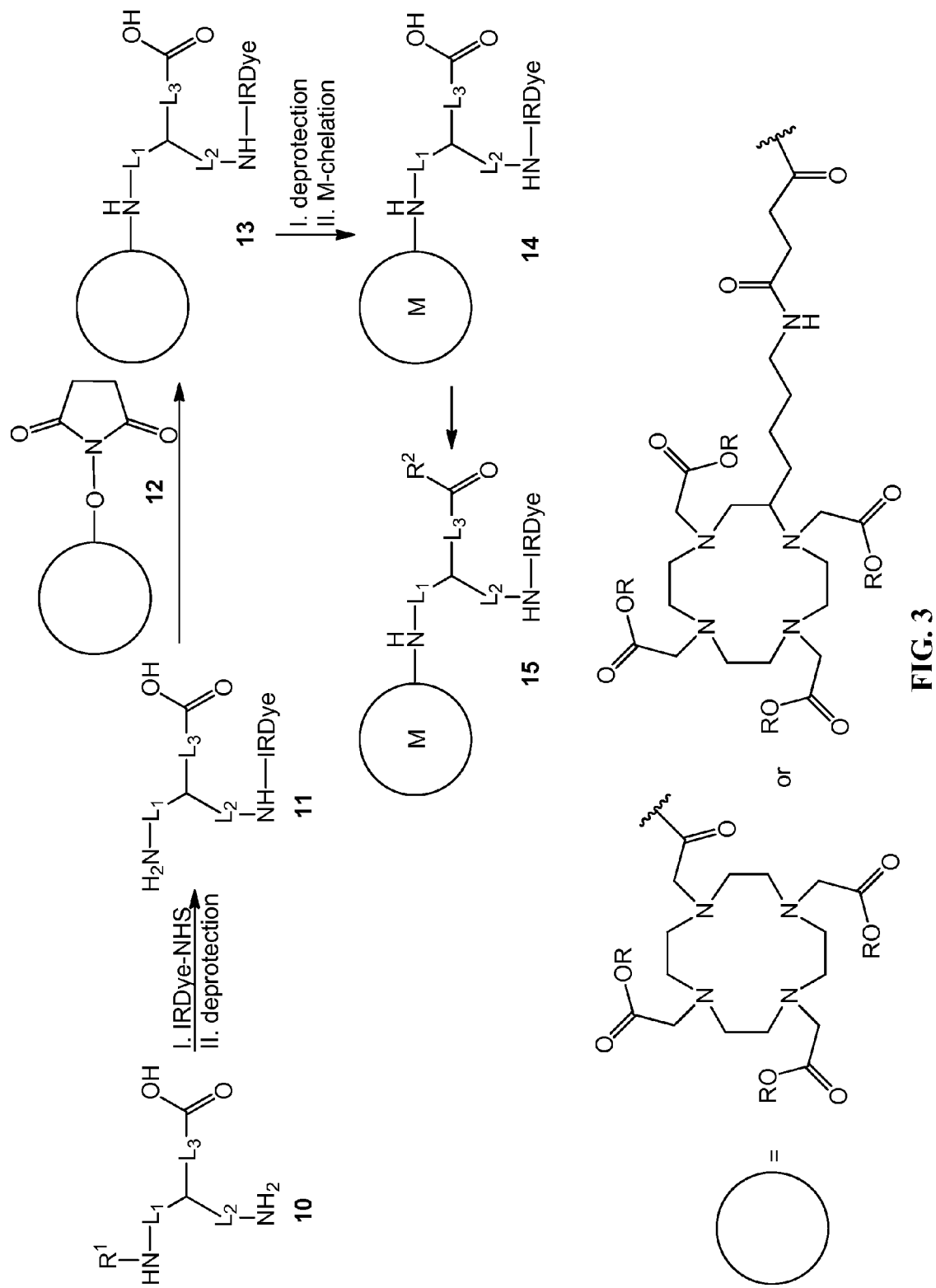
FIG. 3 represents a multimodalilty biotinidase resistant contrast agent in which a NIR fluorophore is conjugated before a metal ion chelation.

FIG. 3 of present invention describes a synthetic scheme for a multimodalilty biotinidase resistant contrast agent in which a NIR fluorophore is conjugated before a metal ion chelation. Reaction of a NIR dye with a trifunctional linker moiety, followed by deprotection of an amino protecting group on a trifunctional linker moiety results in an amino trifunctional linker moiety conjugated NIR dye. Reaction of an organic chelating ligand with an amino trifunctional linker moiety conjugated NIR dye results in a NIR dye containing organic ligand conjugated carboxylic acid precursor. Deprotection of one or more functional groups on a NIR dye containing organic ligand conjugated carboxylic acid precursor yields one or more free functional groups. Chelation of a metal ion on one or more free functional groups results in a NIR dye containing metal chelate conjugated carboxylic acid precursor. Reaction of a biotinidase resistant targeting ligand with a NIR dye containing metal chelate conjugated carboxylic acid precursor results in a multimodalilty biotinidase resistant contrast agent.

Figure 4:
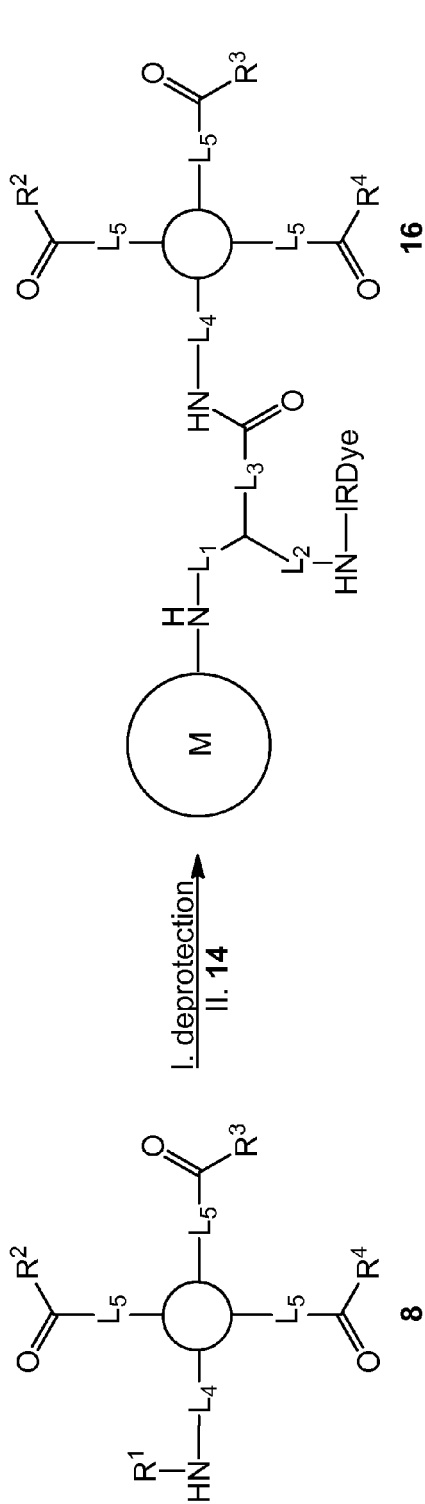
FIG. 4 represents a multimeric multimodalilty biotinidase resistant contrast agent in which a NIR fluorophore is conjugated before a metal ion chelation.
Figure 4:
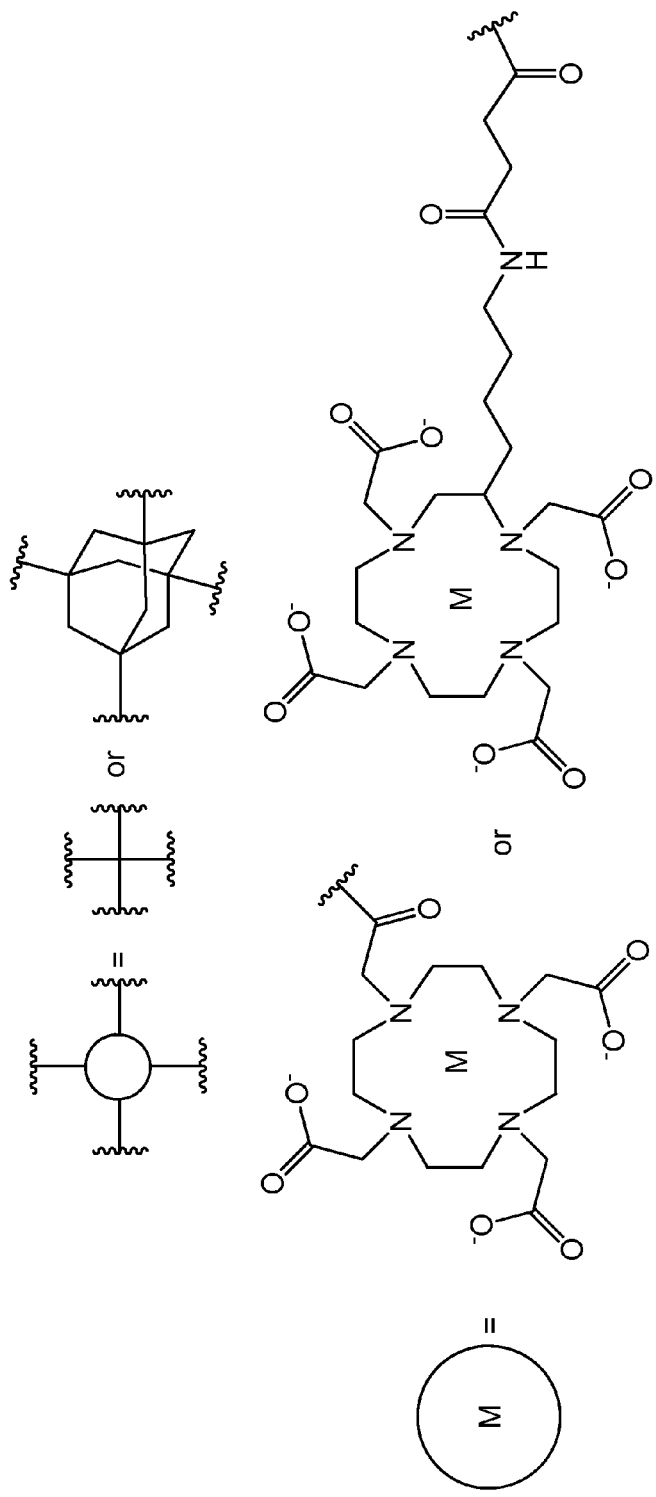
Figure 5:
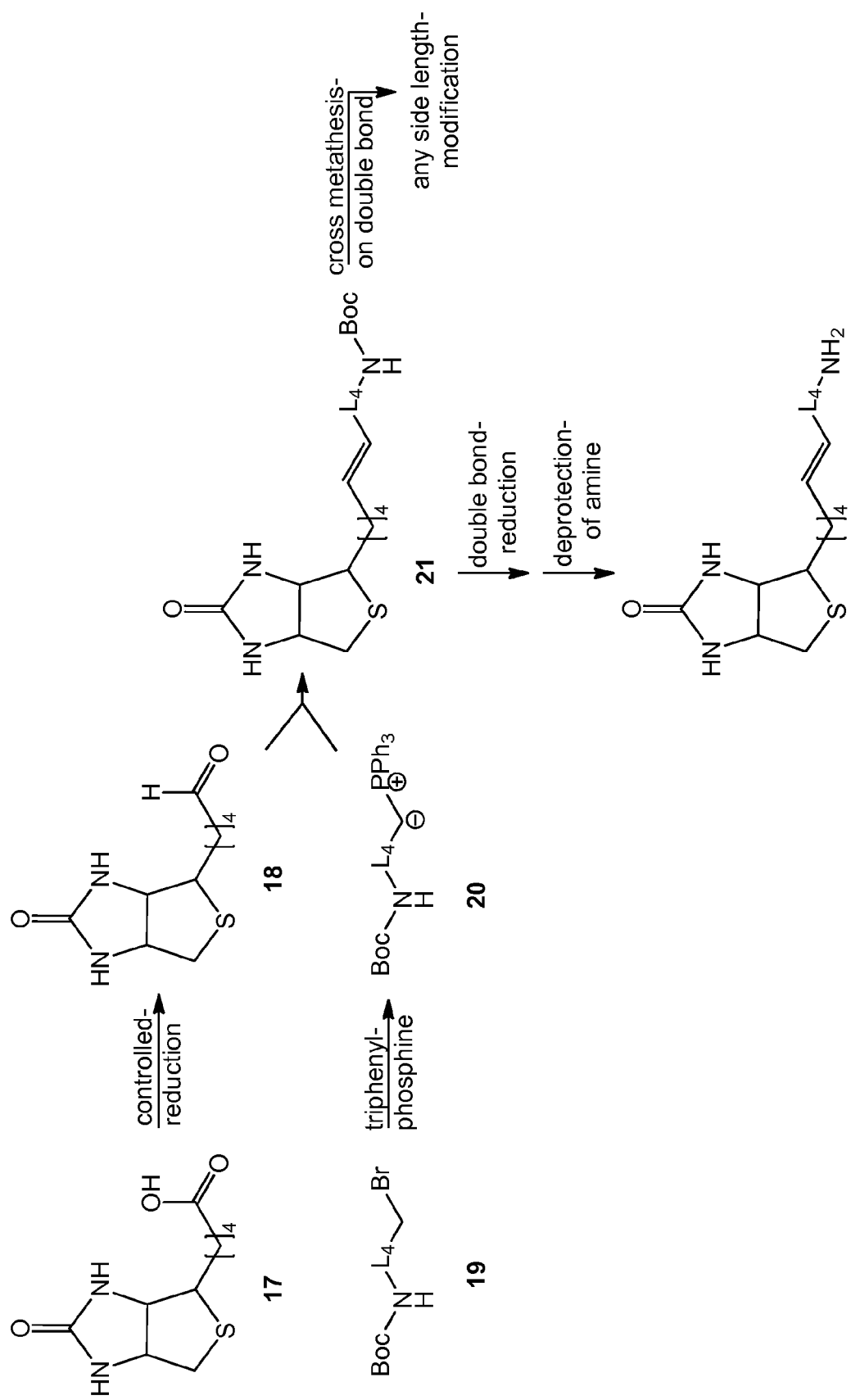
FIG. 5 represents a synthetic scheme for preparation of biotinidase resistant targeting ligand.

FIG. 4 of present invention describes a synthetic scheme for a multimeric multimodalilty biotinidase resistant contrast agent in which a NIR fluorophore is conjugated before a metal ion chelation. A biotinidase resistant targeting ligand is conjugated with multivalent scaffold (FIG. 2), followed by deprotection of an amino protecting group to generate an amine containing biotinidase resistant targeting ligand conjugated multivalent scaffold. Reaction of an amine containing biotinidase resistant targeting ligand conjugated multivalent scaffold with a NIR dye containing metal chelate conjugated carboxylic acid precursor 14 (FIG. 3) results in a multimeric multimodalilty biotinidase resistant contrast agent.

In one aspect, the present invention provides a multimeric multimodalilty biotinidase resistant contrast agent having a formula selected from the group of:

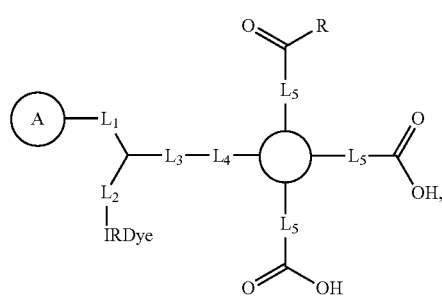

-continued
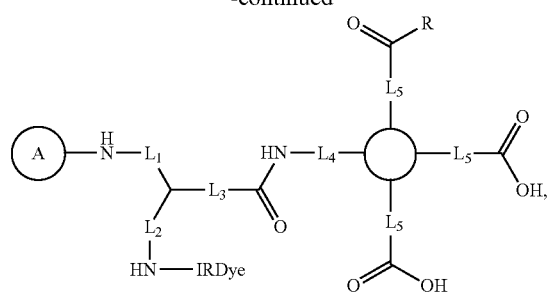
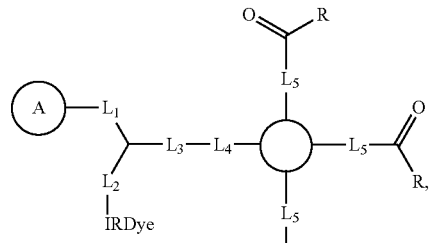
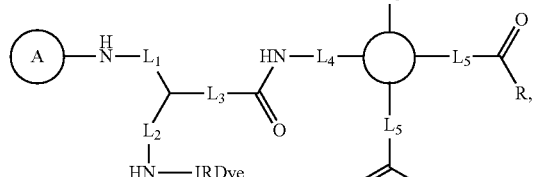
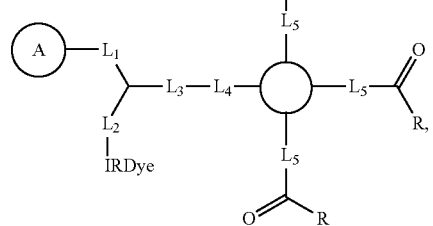
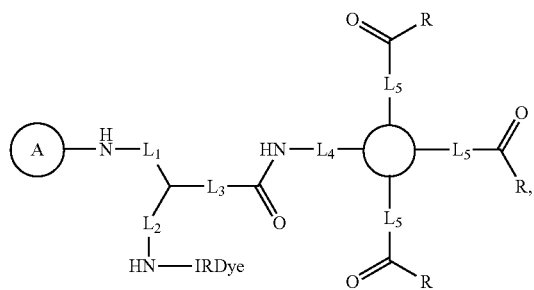
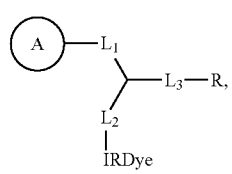 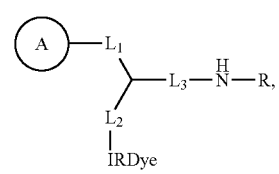
-continued
,
, and
, where
 is  or ,
R is ,
X is  or ,
Y is , ,  or
,
$L_1$, $L_2$, $L_3$, $L_4$, $L_5$ and $L_6$ are linkers,
$R^1$ is a functional probe,
IRDye is a NIR dye with wavelength in the range of 700-900 nm,
and is a metal chelate independently selected from:

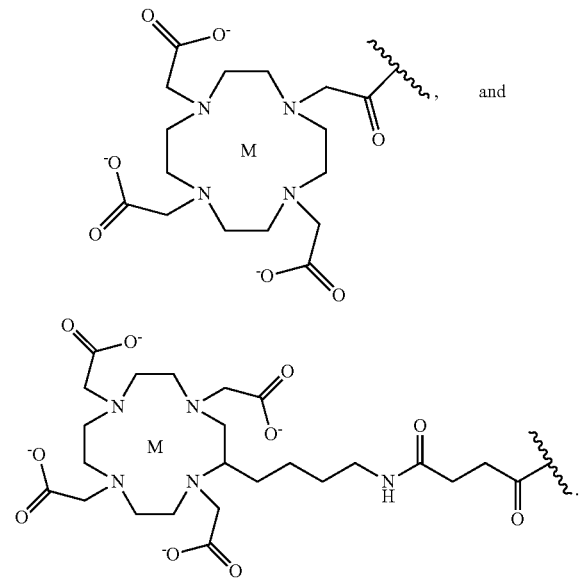

and

In one embodiment, linkers are independently selected from alkane, amino acid, —NHCO(CH$_2$)$_5$—, polyethylene glycol, and polypropylene glycol. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, M is independently selected from Cu, Fe, In, Tm, Yb, Y, Gd, Eu, and a lanthanide. In some embodiments, NIR dye is independently selected from the group of IRDye 78, IRDye 800CW, IRDye 700DX, VivoTag-S 750, VivoTag 800, VivoTag-S 680, DY-750, DY-682, DY-675, Cypate, Cy7, Alexa Fluor 750, and Alexa Fluor 680. In some embodiments, R$^1$ is independently selected from NIR dye and metal chelate. In some embodiments, R$^2$ is independently selected from alkyl, alkenyl, alkynyl, phenyl, benzyl, halo, hydroxyl, carbonyl, aldehyde, carboxylate, ester, ether, amine, nitro, nitrile, and pyridyl.

In an another aspect, the present invention provides a method of making a biotinidase resistant contrast agent. The method involves steps of:

(a) starting synthesis with an organic chelating ligand selected from the group of:

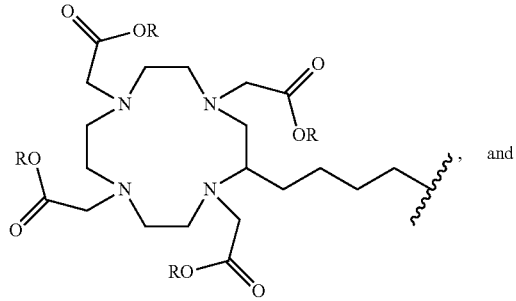

and

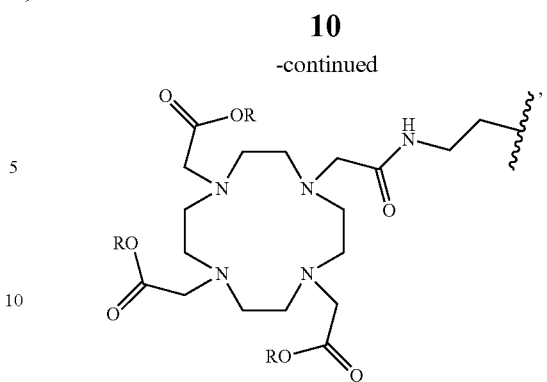

where, R is t-butyl ester, ester, or hydrogen, (b) reacting said organic chelating ligand with a trifunctional linker moiety to result in a trifunctional linker moiety conjugated organic chelating ligand, (c) deprotecting one or more functional groups on a trifunctional linker moiety conjugated organic chelating ligand to yield one or more free functional groups, (d) chelating a metal ion on one or more free functional groups to result in a metal chelate, (e) conjugating a NIR fluorophore with a metal chelate to result a NIR dye containing metal chelate conjugated carboxylic acid precursor, (f) providing a multivalent scaffold independently selected from the group of:

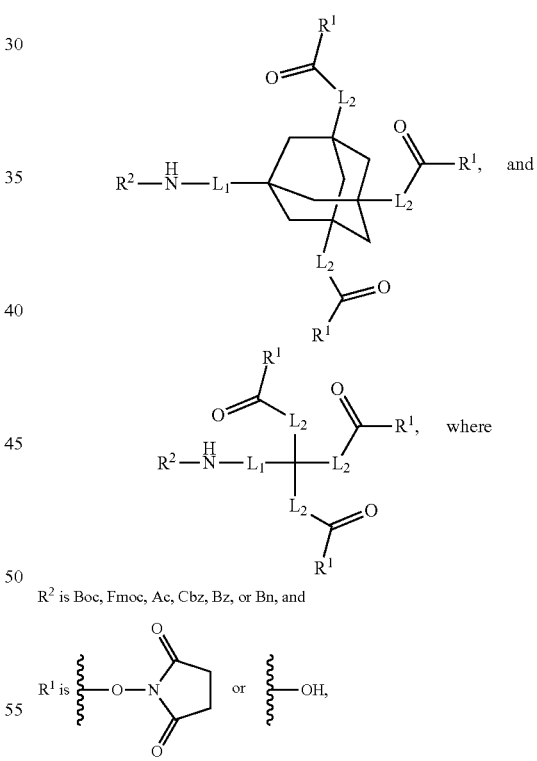

(g) conjugating a multivalent scaffold with a biotinidase resistant targeting ligand to yield one or more biotinidase resistant targeting ligands conjugated multivalent scaffold, (h) deprotecting an amino protecting group on one or more biotinidase resistant targeting ligands conjugated multivalent scaffold to obtain an amine containing biotinidase resistant targeting ligand conjugated multivalent scaffold, and (i) reacting an amine containing biotinidase resistant targeting ligand conjugated multivalent scaffold with a NIR dye containing metal chelate conjugated carboxylic acid precursor to result in a biotinidase resistant contrast agent.

In one embodiment, trifunctional linker moiety is amino acid, polymer, or dendrimer. In some embodiments, metal ion is independently selected from Cu, Fe, In, Tm, Yb, Y, Gd, Eu, and a lanthanide. In some embodiments, a biotinidase resistant targeting ligand is selected from the group of:

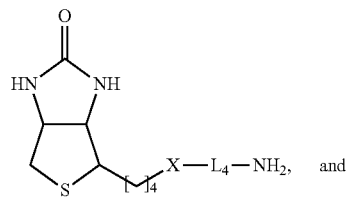

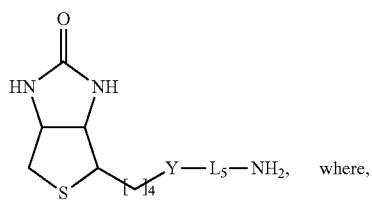

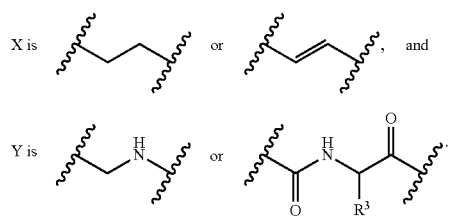

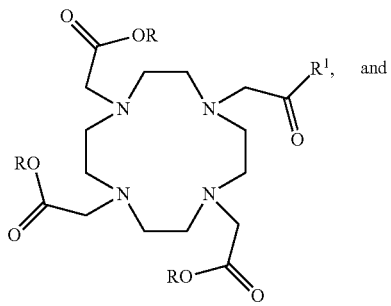

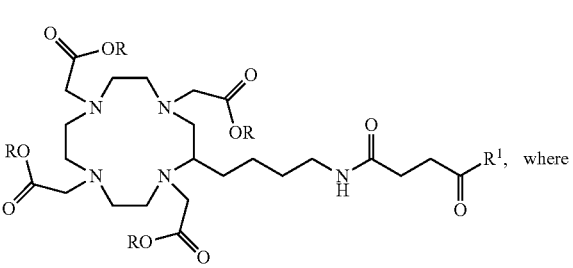

R is t-butyl ester, ester, or hydrogen, and

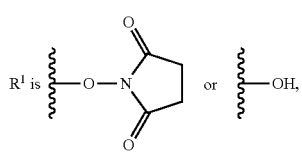

In some embodiments, $L_1$, $L_2$, $L_4$ and $L_5$ are independently selected from alkane, polyethylene glycol, and polypropylene glycol. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, $R^3$ is independently selected from alkyl, alkenyl, alkynyl, phenyl, benzyl, halo, hydroxyl, carbonyl, aldehyde, carboxylate, ester, ether, amine, nitro, nitrile, and pyridyl. In some embodiments, NIR fluorophore is independently selected from the group of IRDye 78, IRDye 800CW, IRDye 700DX, VivoTag-S 750, VivoTag 800, VivoTag-S 680, DY-750, DY-682, DY-675, Cypate, Cy7, Alexa Fluor 750, and Alexa Fluor 680.

In an another aspect, the present invention provides a method of making a biotinidase resistant contrast agent. The method involves steps of:

(a) reacting a NIR dye with a trifunctional linker moiety to result in a trifunctional linker moiety conjugated NIR dye, (b) deprotecting an amino protecting group on a trifunctional linker moiety conjugated NIR dye to result in an amino trifunctional linker moiety conjugated NIR dye, (c) providing an organic chelating ligand selected from the group of:

(d) reacting an organic chelating ligand with an amino trifunctional linker moiety conjugated NIR dye to result in a NIR dye containing organic ligand conjugated carboxylic acid precursor, (e) deprotecting one or more functional groups on a NIR dye containing organic ligand conjugated carboxylic acid precursor to yield one or more free functional groups, (f) chelating a metal ion on one or more free functional groups to result in a NIR dye containing metal chelate conjugated carboxylic acid precursor, (g) providing a multivalent scaffold selected from the group of:

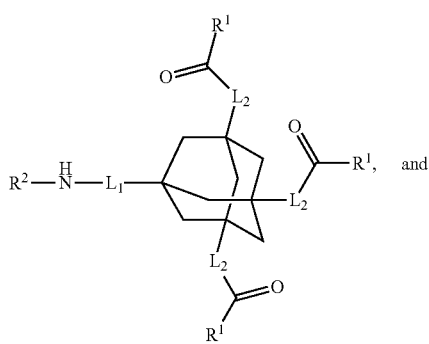

-continued

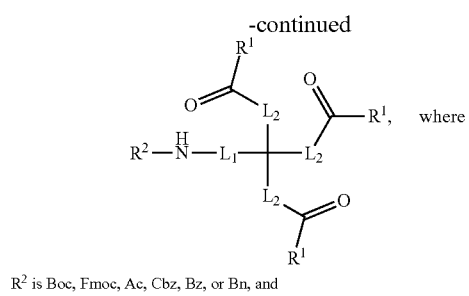

where $R^2$ is Boc, Fmoc, Ac, Cbz, Bz, or Bn, and

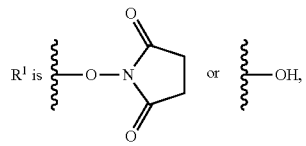

(h) conjugating a multivalent scaffold with a biotinidase resistant targeting ligand to yield one or more biotinidase resistant targeting ligands conjugated multivalent scaffold, (i) deprotecting an amino protecting group on one or more biotinidase resistant targeting ligands conjugated multivalent scaffold to obtain an amine containing biotinidase resistant targeting ligand conjugated multivalent scaffold, and (j) reacting an amine containing biotinidase resistant targeting ligand conjugated multivalent scaffold with a NIR dye containing metal chelate conjugated carboxylic acid precursor to result in a biotinidase resistant contrast agent.

In one embodiment, trifunctional linker moiety is amino acid, polymer, or dendrimer. In some embodiments, metal ion is independently selected from Cu, Fe, In, Tm, Yb, Y, Gd, Eu, and a lanthanide. In some embodiments, a biotinidase resistant targeting ligand is selected from the group of:

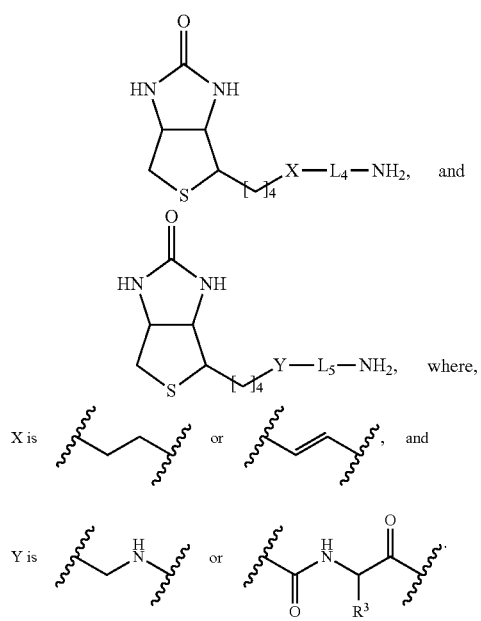

In some embodiments, $L_1$, $L_2$, $L_4$ and $L_5$ are independently selected from alkane, polyethylene glycol, and polypropylene glycol. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, $R^3$ is independently selected from alkyl, alkenyl, alkynyl, phenyl, benzyl, halo, hydroxyl, carbonyl, aldehyde, carboxylate, ester, ether, amine, nitro, nitrile, and pyridyl. In some embodiments, NIR dye is independently selected from the group of IRDye 78, IRDye 800CW, IRDye 700DX, VivoTag-S 750, VivoTag 800, VivoTag-S 680, DY-750, DY-682, DY-675, Cypate, Cy7, Alexa Fluor 750, and Alexa Fluor 680.

With high quantum yields, the spectral properties of multimodality biotinidase resistant contrast agents demonstrates peak absorptions (770-790 nm) and emission (790-810 nm), located within the "NIR window," an area of the electromagnetic spectrum that maximizes photon penetration and recovery in living tissue.

The multimeric multimodality probes generated by present invention can be used for, e.g., optical, MR, radioimmuno, PET, and SPECT applications for direct or pre-targeted diagnosis and therapy of tumors by biotinidase blocking agents. In particular, multimeric biotinidase resistant multimodality probes generated by present invention are (strept)avidin specific and have good serum stability.

The biotinidase stability of biotin resistant biotin derivative (BRBD) probe 30 ($^{111}$In-DOTA derivative) in serum is found ~80% in 24 h compared to stability in PBS. BRBD probes are highly specific and selective toward (strept)avidin beads than biotin agarose beads.

Examples

Figure 6:
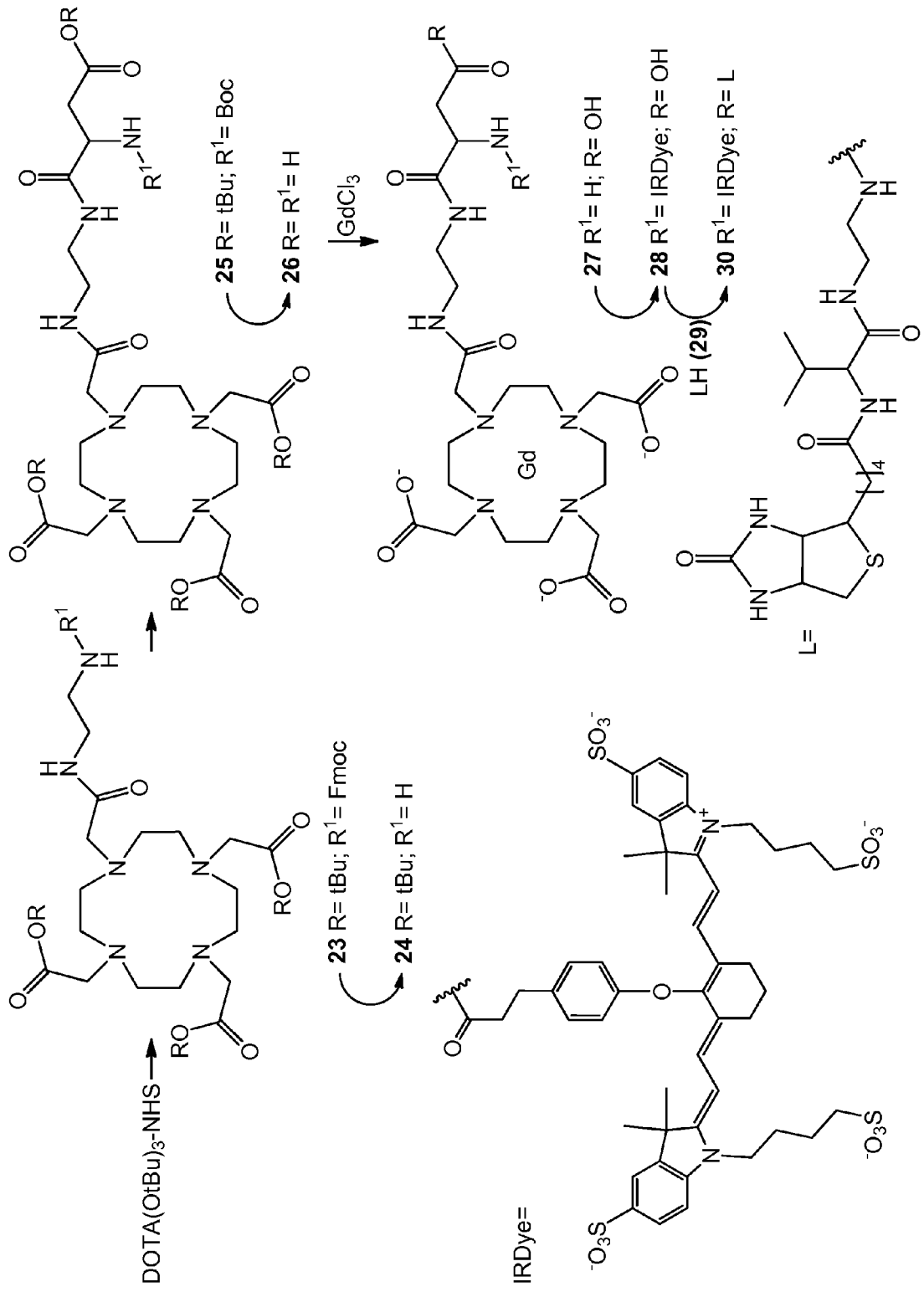
FIG. 6 represents a synthetic scheme for preparation of [Gd-DOTA]-Asp-IRDye-BRBD monomer.

1. Preparation of [Gd-DOTA]-Asp-IRDye-BRBD Monomer (FIG. 6)

DOTA(OtBu)$_3$-Aminoethane

To a solution of Fmoc-1,2-diaminoethane (0.06 mmol) in 0.4 mL DMF at 0° C., is added triethylamine (0.12 mmol) followed by dropwise addition of DOTA(OtBu)$_3$ NHS ester (0.05 mmol) in 0.5 mL DMF for 10 min with stirring. After 10 min, the ice bath is removed and stirring is continued at room temperature (RT) for 6 h. The reaction mixture is poured over 2 mL ice-cold water and purified by preparative HPLC. After concentration and lyophilization, Fmoc amine monomer 23 is obtained which is further treated with 1 mL 20% piperidine in DMF, and the solution is stirred at RT for 30 min. The reaction mixture is poured over 2 mL ice-cold water and purified by preparative HPLC. After lyophilization, DOTA(OtBu)$_3$-aminoethane 24 is obtained.

DOTA(OtBu)$_3$-Boc-Asp-(OtBu)

To a solution of DOTA(OtBu)$_3$-aminoethane 24 (0.06 mmol) in 0.4 mL DMF at 0° C., is added triethylamine (0.12 mmol) followed by dropwise addition of Boc-Asp(OtBu) NHS ester (0.05 mmol) in 0.5 mL DMF for 10 min with stirring. After 10 min, the ice bath is removed and stirring is continued at RT for 6 h. The reaction mixture is poured over 2 mL ice-cold water and purified by preparative HPLC. After concentration and lyophilization, DOTA(OtBu)$_3$-Boc-Asp-(OtBu) 25 is obtained.

DOTA-Asp

DOTA(OtBu)$_3$-Boc-Asp-(OtBu) 25 (0.045 mmol) is taken in 95% TFA (1 mL). The solution is stirred at RT for 6 h then removed the acid by $N_2$ stream. After lyophilization, DOTA-Asp 26 is obtained without further purification as a white powder.

[Gd-DOTA]-Asp

The chelation of $Gd^{3+}$ is performed by adding 50 μL of 1 M $GdCl_3$ in water to a solution of DOTA-Asp 26 (0.04 mmol) in 950 μL of 0.5 M HAc/Ac⁻ buffer (pH 5.5). The reaction mixture is stirred at RT for 12 h. The compound is purified by preparative HPLC to obtain [Gd-DOTA]-Asp 27.

[Gd-DOTA]-Asp-IRDye

To [Gd-DOTA]-Asp 27 (0.01 mmol) in 1 mL DMSO, is added NHS ester of the NIR fluorophore IRDye 78 (IRDye-NHS, 0.01 mmol) and N,N-diisopropylethylamine (0.05 mmol) at 0° C. under nitrogen atmosphere. The stirring is continued for 2 h at RT in the dark. The reaction mixture is poured over 4 mL ice-cold water, purified by HPLC and concentrated on an Oasis HLB desalting cartridge as described previously {Bhushan, 2007}. On lyophilization a bright green solid reaction component, [Gd-DOTA]-Asp-IRDye 28 is obtained.

BRBD Amine

BRBD, a valine adduct (0.05 mmol) {Wilbur, 2006), HCTU (0.05 mmol), and N-methylmorpholine (NMM; 0.20 mmol) are added at RT under $N_2$ atmosphere to 0.05 mmol Boc-1,2-diaminoethane in DMSO (1 mL). After stirring for 3 h at RT, the reaction mixture is poured over 3 mL ice-cold water and an intermediate BRBD amine 29 is purified by preparative HPLC.

[Gd-DOTA]-Asp-IRDye-BRBD Monomer

[Gd-DOTA]-Asp-IRDye 28 (0.01 mmol), HCTU (0.01 mmol), and NMM (0.05 mmol) are added at RT under $N_2$ atmosphere to 0.01 mmol BRBD amine 29 in DMSO (1 mL). After stirring for 2 h at RT in the dark the reaction mixture is poured over 4 mL ice-cold water, purified by HPLC and concentrated on an Oasis HLB desalting cartridge. On lyophilization a bright green solid reaction component, [Gd-DOTA]-Asp-IRDye-BRBD monomer 30 is obtained.

Figure 7:
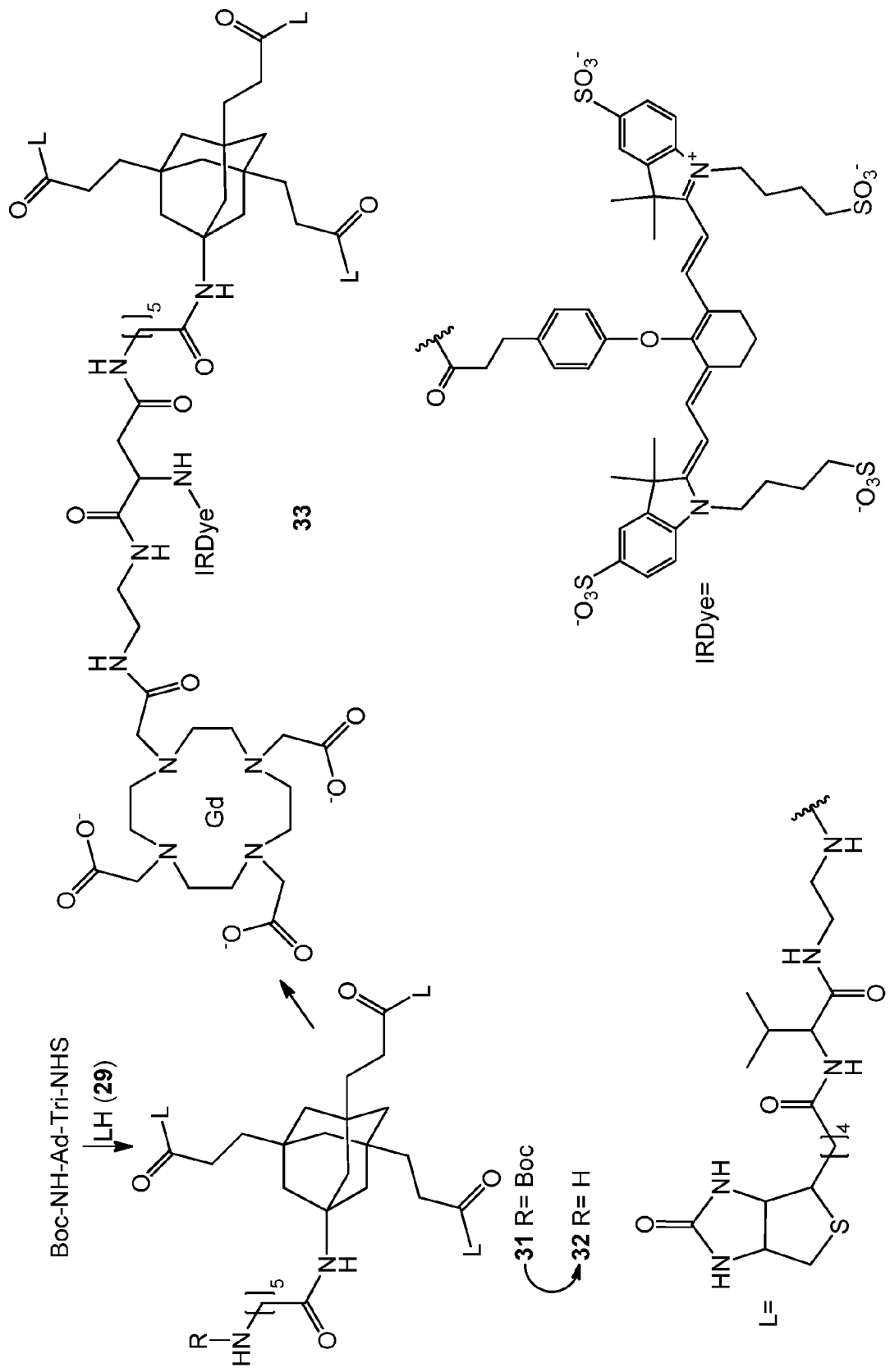
FIG. 7 represents a synthetic scheme for preparation of [Gd-DOTA]-Asp-IRDye-Ad-BRBD trimer.

2. Preparation of [Gd-DOTA]-Asp-IRDye-Ad-BRBD Trimer (FIG. 7)

Ad-BRBD Trimer

BRBD amine 29 (0.06 mmol) is dissolved in 1 mL of DMSO and triethylamine (0.30 mmol). After 5 min, a solution of Boc-NH-Ad-Tri-NHS (0.015 mmol) {Humblet, 2009} in 0.2 mL of DMSO is added. The reaction mixture is stirred at RT for 16 h. The compound 31 is purified after dilution into a final volume of 5 mL with ice-cold water by preparative HPLC system. After lyophilization, product 31 is treated with 95% TFA (1 mL) for 3 h. Excess TFA is removed under nitrogen and after lyophilization the Ad-BRBD trimer 32 is obtained.

[Gd-DOTA]-Asp-IRDye-Ad-BRBD Trimer

To a solution of [Gd-DOTA]-Asp-IRDye 28 (0.01 mmol) in 1 mL DMSO at 0° C., is added HCTU (0.01 mmol) and NMM (0.05 mmol) followed by dropwise addition of Ad-BRBD trimer 32 (0.01 mmol) in 0.5 mL DMF for 10 min with stirring. After 10 min, the ice bath is removed and stirring is continued at RT for 2 h in the dark. The reaction mixture is poured over 2 mL ice-cold water and purified by preparative HPLC to obtain [Gd-DOTA]-Asp-IRDye-Ad-BRBD trimer 33.

3. In Vitro Assessment of BRBD Probes Stability, Specificity and Selectivity

In order to determine in vitro serum stability of BRBD probes in (i) PBS and, (ii) Serum. Equal volume (20% slurry, 150 μl) of (strept)avidin agarose beads and biotin agarose beads are taken in two set of 2 mL eppendorf tube, is washed with buffer for one set and with serum for another set, and is added 65 μci of [$^{111}$In-DOTA] derivative of 30 in each, incubate at 37° C. for 30 min, and is washed with buffer for one set and with serum for another set. Count radioactivity and image is taken on Gamma scintigraphy. Equal amount (1 mL) buffer is added for one set and serum for another set, and left sample at 37° C. for 24 h, washed with buffer for one set and with serum for another set, and activity is measured by Gamma counter.

REFERENCES

1. Rusckowski M, Paganelli G, Hnatowich D J, Magnani P, Virzi F, Fogarasi M, DiLeo C, Sudati F, Fazio F. Imaging osteomyelitis with streptavidin and indium-111-labeled biotin. *J. Nucl. Med*. 1996, 37, 1655-1662.
2. van Gog F B, Visser G W, Gowrising R W, Snow G B, van Dongen G A. Synthesis and evaluation of 99mTc/99Tc-MAG3-biotin conjugates for antibody pretargeting strategie. *Nucl. Med. Biol*. 1998, 25, 611-619.
3. Foulton C F, Alston K L, Zalutsky M R. Astatine-211-labeled biotin conjugates resistant to biotinidase for use in pretargeted radioimmunotherapy. *Nucl. Med. Biol*. 1998, 25, 81-88.
4. Hymes J, Wolf B. Biotinidase and its roles in biotin metabolism. *Clin. Chim. Acta*. 1996, 255, 1-11.
5. Wilbur D S, Hamlin D K, Pathare P M, Weerawarna S A. Biotin reagents for antibody pretargeting. Synthesis, radioiodination, and in vitro evaluation of water soluble, biotinidase resistant biotin derivatives. *Bioconjug. Chem*. 1997, 8, 572-584.
6. Park J M, Gambhir, S S. Multimodality radionuclide, fluorescence, and bioluminescence small-animal imaging. *Proc IEEE* 2005, 93, 771-783.
7. Pietrzyk U, Herholz K, Schuster A, von Stockhausen H M, Lucht H, Heiss W D. Clinical applications of registration and fusion of multimodality brain images from PET, SPECT, CT, and MRI. *Eur. J. Radiol*. 1996, 21, 174-182.
8. Saoudi A, Lecomte R. A novel APD-based detector module for multi-modality PET/SPECT/CT scanners. *IEEE Trans Nucl. Sc*. 1999, 46, 479-484.
9. Weissleder R, Mahmood U. Molecular imaging. *Radiology* 2001, 219, 316-333.
10. Sokolov K, Follen M, Aaron J. Real-time vital optical imaging of precancer using anti-epidermal growth factor receptor antibodies conjugated to gold nanoparticles. *Cancer Res*. 2003, 63, 1999-2004.
11. Ntziachristos V, Bremer C, Weissleder R. Fluorescence imaging with near-infrared light: new technological advances that enable in vivo molecular imaging. *Eur. Radiol*. 2003, 13, 195-208.

12. Gurfinkel M, Ke S, Wen X, Li C, Sevick-Muraca E M. Near-infrared fluorescence optical imaging and tomography. *Dis. Markers* 2003, 19, 107-121.
13. Li H, Gray B D, Corbin I, Lebherz C, et al. MR and fluorescent imagining of low-density lipoprotein receptors. *Acad. Radiol.* 2004, 11, 1251-1259.
14. Massoud T F, Gambhir S S. Molecular imaging in living subjects: seeing fundamental biological processes in a new light. *Genes. Den.* 2003, 17, 545-580.
15. Kitov P I, Bundle D R. On the nature of the multivalency effect: a thermodynamic model. *J. Am. Chem. Soc.* 2003, 125, 16271-16284.
16. Mammen M, Chio S K, Whitesides G M. Polyvalent interactions in biological systems: implications for design and use of multivalent ligands and inhibitors. *Angew. Chem., Int. Ed.* 1998, 37, 2755-2794.
17. Lindhorst T K. Artificial multivalent sugar ligands to understand and manipulate carbohydrate-protein interactions. *Top. Curr. Chem.* 2002, 218, 201-235.
18. Lundquist J J, Toone E J. The cluster glycoside effect. *Chem. Rev.* 2002, 102, 555-578.
19. Wright D, Usher L. Multivalent binding in the design of bioactive compounds. *Curr. Org. Chem.* 2001, 5, 1107-1131.
20. Carlson C, Mowery P, Owen R, Dykhuizen E, Kiessling, L. Selective tumor cell targeting using low-affinity, multivalent interactions. *ACS Chem. Biol.* 2007, 2, 119-127.
21. Thumshirn G, Hersel U, Goodman S L, Kessler H. Multimeric cyclic RGD peptides as potential tools for tumor targeting: solid-phase peptide synthesis and chemoselective oxime ligation. *Chem. Eur. J.* 2003, 9, 2717-2725.
22. Voegtle F, Richardt G, Werner N. *Dendritische Moleküle*; B. G. Teubner Verlag: Wiesbaden, Germany, 2007.
23. Haag R, Kratz F. Polymer therapeutics: concepts and applications. *Angew. Chem. Int. Ed.* 2006, 45, 1198-1215.
24. Pispa, J. Animal biotinidase. *Ann. Med. Exp. Biol. Fenn.* 1965, 43, 1-39.
25. Foulton C F, Alston K L, Zalutsky M R. Synthesis and preliminary biological evaluation of (3-iodobenzoyl)norbiotinamide and [(5-iodo-3-pyridinyl)carbonyl]norbiotinamide: two radioiodinated biotin conjugates with improved stability. *Bioconjug. Chem.* 1997, 8, 179-186.
26. Wilbur D S, Hamlin D K, Chyan M K. Biotin reagents for antibody pretargeting. 7. Investigation of chemically inert biotinidase blocking functionalities for synthetic utility. *Bioconjug. Chem.* 2006, 17, 1514-1522.
27. Sabatino S, Chinol M, Paganelli G, et al. A new biotin derivative-DOTA conjugate as a candidate for pretargeted diagnosis and therapy of tumor. *J. Med. Chem.* 2003, 46, 3170-3173.
28. Bhushan K R, Tanaka E, Franbioni J V. Synthesis of conjugatable bisphosphonates for molecular imaging of large animals. *Angew. Chem. Int. Ed. Engl.* 2007, 46, 7969-7971.
29. Humblet V, Misra P, Bhushan K R, et al. Multivalent scaffolds for affinity maturation of small molecule cell surface binders and their application to prostate tumor targeting. *J. Med. Chem.* 2009, 52, 544-550.

What is claimed is:

1. A biotinidase resistant contrast agent having a formula selected from the group consisting of:

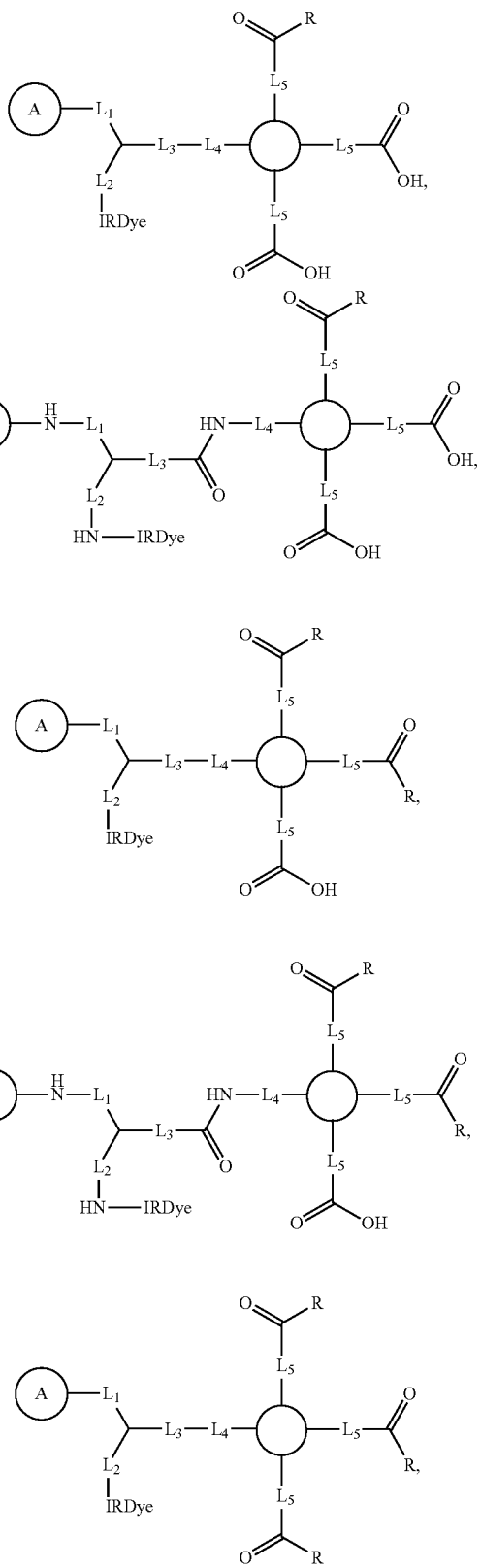

-continued

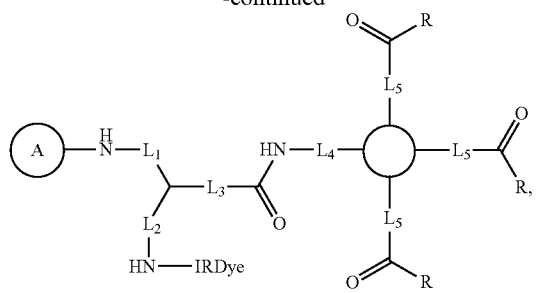

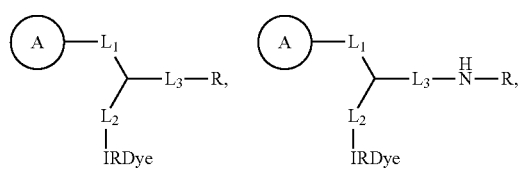

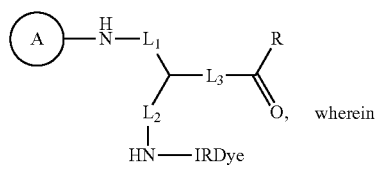

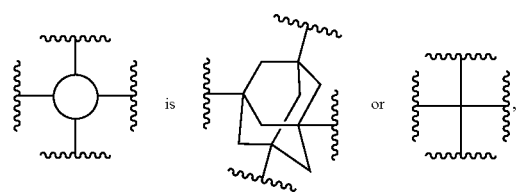

R is 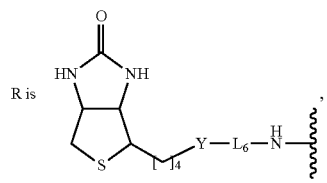

Y is 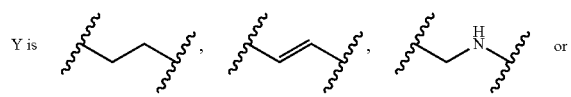 or

, $L_1$, $L_2$, $L_3$, $L_4$, $L_5$ and $L_6$ are linkers, $R^2$ is a functional group, wherein said functional group is independently selected from alkyl, alkenyl, alkynyl, phenyl, benzyl, halo, hydroxyl, carbonyl, aldehyde, carboxylate, ester, ether, amine, nitro, nitrile, and pyridyl, IRDye is a near infrared dye with wavelength in the range of 700-900 nm, and

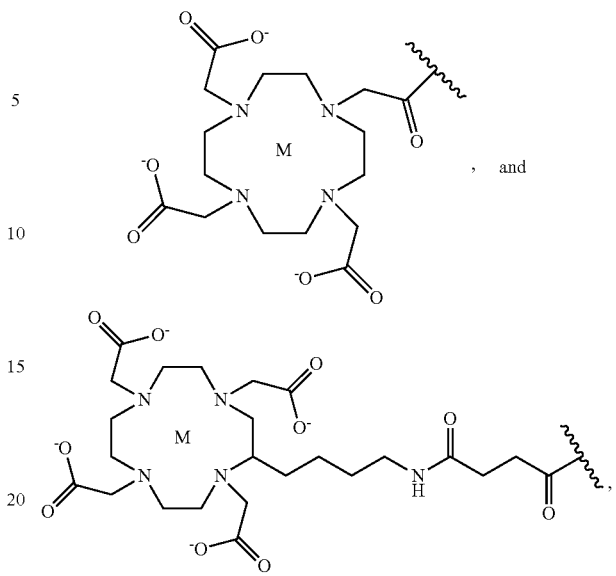

is a metal chelate.

2. The biotinidase resistant contrast agent of claim 1, wherein said linkers are selected from the group consisting of alkane, amino acid, —NHCO(CH$_2$)$_5$—, polyethylene glycol, and polypropylene glycol.

3. The biotinidase resistant contrast agent of claim 1, wherein said near infrared dye is selected from the group consisting of IRDye 78, IRDye 800CW, IRDye 700DX, VivoTag-S 750, VivoTag 800, VivoTag-S 680, DY-750, DY-682, DY-675, Cypate, Alexa Fluor 750, and Alexa Fluor 680.

4. A method of making a biotinidase resistant contrast agent, said method comprising:
   providing an organic chelating ligand, wherein said organic chelating ligand selected from the group of:

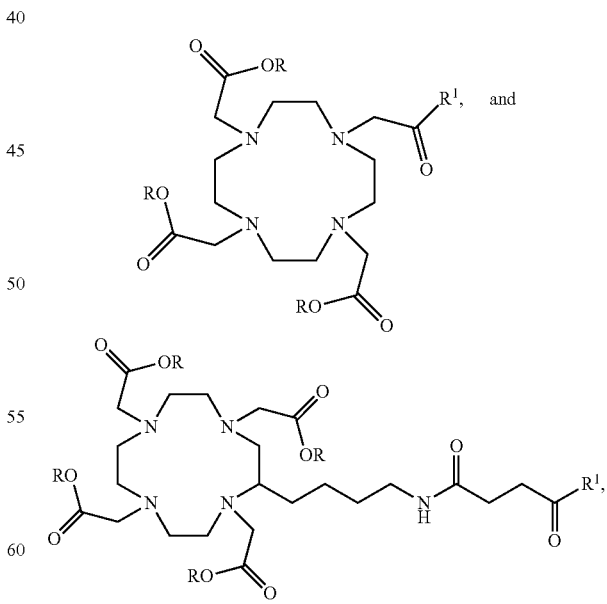

wherein R is t-buty ester, ester, or hydrogen;
   reacting said organic chelating ligand with a trifunctional linker moiety to result in a trifunctional linker moiety conjugated organic chelating ligand;

deprotecting one or more functional groups on said trifunctional linker moiety conjugated organic chelating ligand to yield one or more free functional groups;

chelating a metal ion on said one or more free functional groups to result in a metal chelate;

conjugating a near infrared fluorophore with said metal chelate to result a near infrared dye containing metal chelate conjugated carboxylic acid precursor;

providing a multivalent scaffold, wherein said multivalent scaffold is selected from the group of:

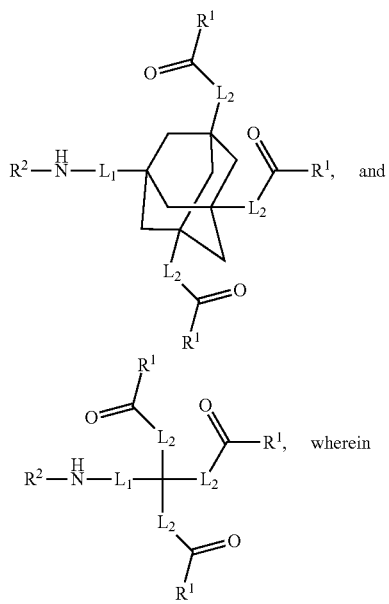

$R^2$ is Boc, Fmoc, Ac, Cbz, Bz, or Bn,
$L_1$ and $L_2$ are linkers, and

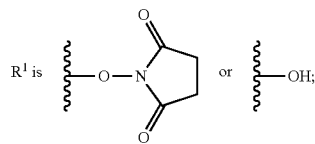

conjugating said multivalent scaffold with a biotinidase resistant targeting ligand to yield one or more biotinidase resistant targeting ligands conjugated multivalent scaffold;

deprotecting an amino protecting group on said one or more biotinidase resistant targeting ligands conjugated multivalent scaffold to obtain an amine containing biotinidase resistant targeting ligand conjugated multivalent scaffold; and reacting said amine containing biotinidase resistant targeting ligand conjugated multivalent scaffold with said near infrared dye containing metal chelate conjugated carboxylic acid precursor to result in said biotinidase resistant contrast agent.

5. The method of claim 4, wherein said trifunctional linker moiety is amino acid, polymer, or dendrimer.

6. The method of claim 4, wherein said near infrared fluorophore is selected from the group consisting of IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

7. The method of claim 4, wherein said metal ion is selected from the group consisting of Cu, Fe, In, Mn, Tm, Yb, Y, Gd, Eu, and a lanthanide.

8. The method of claim 4, wherein said metal ion and said near infrared fluorophore are conjugated for concurrent magnetic resonance and near infrared optical imaging.

9. The method of claim 4, wherein said metal ion and said near infrared fluorophore are conjugated for concurrent nuclear and near infrared optical imaging.

10. The method of claim 4, wherein said biotinidase resistant targeting ligand is selected from the group consisting of

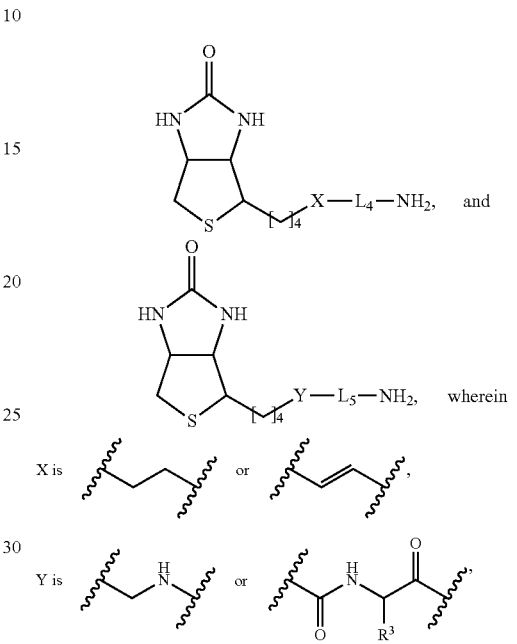

$L_4$ and $L_5$ are linking moiety, and $R^3$ is independently selected from alkyl, alkenyl, allynyl, phenyl, benzyl, halo, hydroxyl, carbonyl, aldehyde, carboxylate, ester, ether, amine, nitro, nitrile, and pyridyl.

11. A method of making a biotinidase resistant contrast agent, said method comprising:

reacting a near infrared dye with a trifunctional linker moiety to result in a trifunctional linker moiety conjugated near infrared dye;

deprotecting an amino protecting group on said trifunctional linker moiety conjugated near infrared dye to result in an amino trifunctional linker moiety conjugated near infrared dye;

providing an organic chelating ligand, wherein said organic chelating ligand selected from the group of:

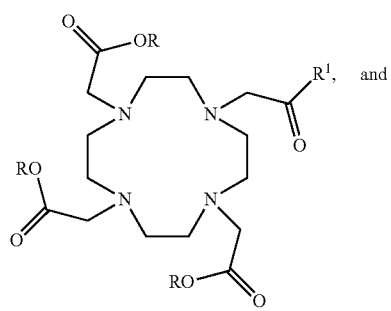

-continued

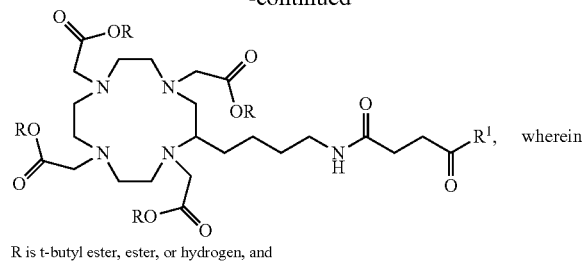

R is t-butyl ester, ester, or hydrogen, and

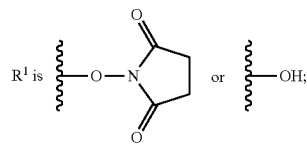

reacting said organic chelating ligand with said amino trifunctional linker moiety conjugated near infrared dye to result in a near infrared dye containing organic ligand conjugated carboxylic acid precursor;

deprotecting one or more functional groups on said near infrared dye containing organic ligand conjugated carboxylic acid precursor to yield one or more free functional groups;

chelating a metal ion on said one or more free functional groups to result in a near infrared dye containing metal chelate conjugated carboxylic acid precursor;

providing a multivalent scaffold, wherein said multivalent scaffold is selected from the group of:

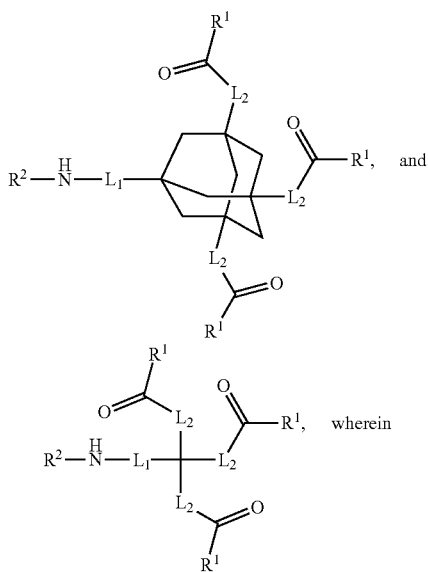

$R^2$ is Boc, Fmoc, Ac, Cbz, Bz, or Bn, $L_1$ and $L_2$ are linkers, and

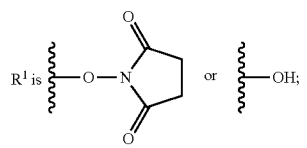

conjugating said multivalent scaffold with a biotinidase resistant targeting ligand to yield one or more biotinidase resistant targeting ligands conjugated multivalent scaffold;

deprotecting an amino protecting group on said one or more biotinidase resistant targeting ligands conjugated multivalent scaffold to obtain an amine containing biotinidase resistant targeting ligand conjugated multivalent scaffold; and reacting said amine containing biotinidase resistant targeting ligand conjugated multivalent scaffold with said near infrared dye containing metal chelate conjugated carboxylic acid precursor to result in said biotinidase resistant contrast agent.

12. The method of claim 11, wherein said trifunctional linker moiety is amino acid, polymer, or dendrimer.

13. The method of claim 11, wherein said near infrared dye is selected from the group consisting of IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

14. The method of claim 11, wherein said metal ion is selected from the group consisting of Cu, Fe, In, Mn, Tm, Yb, Y, Gd, Eu, and a lanthanide.

15. The method of claim 11, wherein said biotinidase resistant contrast agent is in a form of pharmaceutically acceptable salts, hydrates, and solvates.

16. The method of claim 11, wherein said biotinidase resistant targeting ligand is selected from the group consisting of:

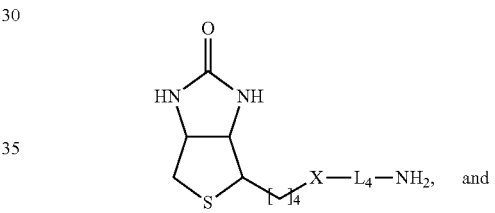

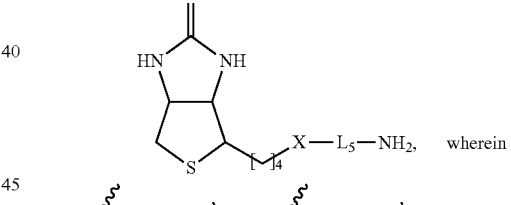

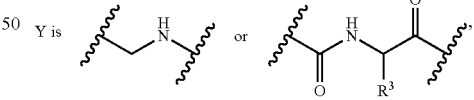

$L_4$ and $L_5$ are linking moiety, and $R^3$ is independently selected from alkyl, alkenyl, alkynyl, phenyl, benzyl, halo, hydroxyl, carbonyl, aldehyde, carboxylate, ester, ether, amine, nitro, nitrile, and pyridyl.

17. The method of claim 11, wherein said a biotinidase resistant targeting ligand is reacted with said near infrared dye containing metal chelate conjugated carboxylic acid precursor to obtain said biotinidase resistant contrast agent.

* * * * *